United States Patent [19]

Kropp et al.

[11] 4,320,062
[45] Mar. 16, 1982

[54] PREPARATION OF 5-(2,2,2-TRIHALOETHYL)-DIALKYL-TETRAHYDROFURAN-2-ONES

[75] Inventors: Rudolf Kropp, Limburgerhof; Martin Fischer, Ludwigshafen; Klaus Halbritter, Mannheim, all of Fed. Rep. of Germany

[73] Assignee: BASF Aktiengesellschaft, Fed. Rep. of Germany

[21] Appl. No.: 178,171

[22] Filed: Aug. 14, 1980

[30] Foreign Application Priority Data

Sep. 19, 1979 [DE] Fed. Rep. of Germany ....... 2937836

[51] Int. Cl.³ ............................................ C07D 307/32
[52] U.S. Cl. ......................... 260/343.6; 260/326.5 D; 260/347.7; 544/152; 546/214; 204/158 R; 204/158 HA
[58] Field of Search .......... 260/343.6, 347.7, 326.5 D; 546/214; 544/152; 204/158, 158 HA

[56] References Cited

U.S. PATENT DOCUMENTS 3,884,916 5/1975 Janssen et al. ................... 260/347.7
4,215,050 7/1980 Lantzsch .......................... 260/343.6

FOREIGN PATENT DOCUMENTS 52-83456 7/1977 Japan ............................... 260/343.6

OTHER PUBLICATIONS

Chemical Abstracts Vol. 87, 200815c (1977)

Primary Examiner—Henry R. Jiles
Assistant Examiner—Jane T. Fan
Attorney, Agent, or Firm—Keil & Witherspoon

[57] ABSTRACT

Preparation of 5-(2,2,2-trihaloethyl)-4,4-dialkyl-tetrahydro-furan-2-ones of the formula I

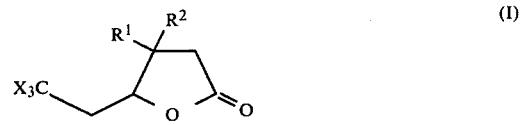

where $R^1$ and $R^2$ are each alkyl of 1 to 4 carbon atoms and X is halogen, by reacting a carboxylic acid amide of the formula II

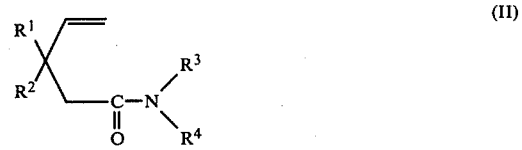

where $R^3$ and $R^4$ are each alkyl of 1 to 4 carbon atoms, aralkyl of 7 to 9 carbon atoms or aryl of 6 to 10 carbon atoms or together with the nitrogen on which they are present as substituents form a 5-membered or 6-membered saturated ring which may contain a second hetero-atom, with a carbon tetrahalide of the formula III

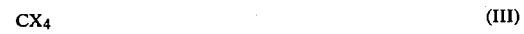

to give an iminium salt of the formula IV

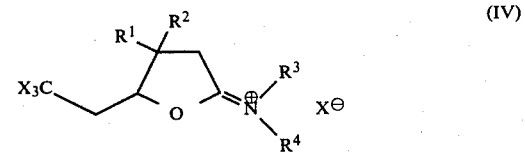

and subsequently hydrolyzing this iminium salt; and novel iminium salts of the formula IV.

3 Claims, No Drawings

PREPARATION OF 5-(2,2,2-TRIHALOETHYL)-DIALKYL-TETRAHYDROFURAN-2-ONES

The present invention relates to a process for the preparation of 5-(2,2,2-trihaloethyl)-4,4-dialkyltetrahydrofuran-2-ones by reacting N,N-disubstituted carboxylic acid amides with carbon tetrahalides and then hydrolyzing the iminium salts obtained.

The preparation of 5-(2,2,2-trichloroethyl)-4,4-dimethyl-tetrahydrofuran-2-ones by an addition reaction of 3,3,3-trichloropropanol with 3,3-dimethylacrylic acid esters and subsequent dehydrochlorination is known (Japanese Laid-Open Application Ser. No. 77/83,456). Disadvantages of this process are the low yield and the difficulty of obtaining the starting material 3,3,3-trichloropropanol.

We have found that 5-(2,2,2-trihaloethyl)-4,4-dialkyl-tetrahydrofuran-2-ones of the formula

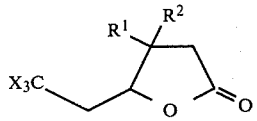

(I)

wherein $R^1$, and $R^2$ are each alkyl of 1 to 4 carbon atoms and X is halogen are obtained in an advantageous manner when a carboxylic acid amide of the formula II

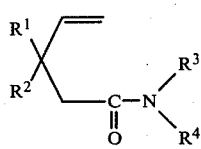

(II)

where $R^1$ and $R^2$ are each alkyl of 1 to 4 carbon atoms and $R^3$ and $R^4$ are each alkyl of 1 to 4 carbon atoms, aralkyl of 7 to 9 carbon atoms or aryl of 6 to 10 carbon atoms, or together with the nitrogen atom on which they are present as substituents form a 5-membered or 6-membered saturated ring which may contain a further hetero-atom, is reacted with a carbon tetrahalide of the formula III $$CX_4 \quad (III)$$

where X is halogen, in the presence of an initiator and of an organic diluent or solvent, at from room temperature to 120° C., to give an iminium salt of the formula IV

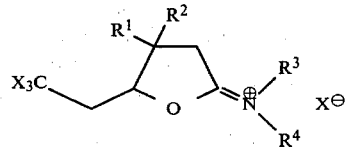

(IV)

where $R^1$, $R^2$, $R^3$, $R^4$ and X have the above meanings, and this iminium salt is subsequently hydrolyzed.

The novel process may be used to prepare 5-(2,2,2-trihaloethyl)-4,4-dialkyl-tetrahydrofuran-2-ones which serve as intermediates for the synthesis of active ingredients of insecticides. The compounds can be converted, by elimination of hydrogen halide, for example by means of an alkali metal alcoholate or by heating, and by treatment with an inorganic acid halide, for example a thionyl halide, followed by reaction with a base, to 2-(2,2-dihalovinyl)-3,3-dialkyl-cyclopropanecarboxylic acid esters (German Laid-Open Application DOS No. 2,621,831), of which the alkyl 2-(2,2-dihalovinyl)-3,3-dimethylcyclopropanecarboxylates, in particular, are starting materials for the synthesis of pyrethroid-type active ingredients of insecticides. The synthesis of the 5-(2,2,2-trihaloethyl)-4,4-dialkyl-tetrahydrofuran-2-ones by the novel process is particularly advantageous and economical since the desired products are obtained from easily obtainable starting materials in good yields by a method which is simple to operate industrially.

The carboxylic acid amides of the formula II used as starting materials are known and may be prepared by methods based on conventional processes (Japanese Laid-Open Application Ser. No. 77/83,411; German Laid-Open Application DOS No. 2,732,213). The starting materials of the formula II can also be obtained by reaction of an acetamide-acetal or ketene-acetal-aminal with 3-methyl-but-2-en-1-ol.

Preferred starting materials of the formula II are 3,3-dimethyl-pent-4-enoic acid N,N-dimethylamide, 3,3-diethyl-pent-4-enoic acid N,N-dimethylamide, 3-methyl-3-n-propyl-pent-4-enoic acid N,N-dimethylamide, 3,3-dimethyl-pent-4-enoic acid N-methyl-N-phenylamide, 3,3-dimethyl-pent-4-enoic acid N-methyl-N-benzylamide, 3,3-dimethyl-pent-4-enoic acid pyrrolidide and 3,3-dimethyl-pent-4-enoic acid morpholide.

Examples of suitable carbon tetrahalides of the formula III are carbon tetrachloride, carbon tetrabromide and bromotrichloromethane.

The starting materials of the formulae II and III may be reacted in stoichiometric amounts. However, it is advantageous to employ the starting material of the formula III in excess, ie. in general in an amount of from 1 to 20 moles, advantageously from 3 to 10 moles, per mole of starting material of the formula II.

Suitable initiators for the reaction of the carboxylic acid amides with the carbon tetrahalides to give iminium salts are organic peroxides or per-esters, eg. di-tert.-butyl peroxide, dibenzoyl peroxide or tert.-butyl 2-ethyl-hexanepercarboxylate, azo-bis-isobutyronitrile or Redox systems which contain iron ions and/or copper ions, eg. $Fe^{3+}/Fe^{2+}$, $Cu^{2+}/Cu^{1+}$ or $Cu^{2+}/Fe^{2+}$; ultraviolet light may also be used to initiate the reaction. From 0.01 to 0.5 mole, preferably from 0.05 to 0.2 mole, of initiator is added per mole of carboxylic acid amide of the formula II.

Suitable organic diluents and solvents are aliphatic and aromatic hydrocarbons and chlorohydrocarbons, eg. heptane, cyclohexane, benzene, toluene and chlorobenzene. However, it is advantageous to use an excess of the carbon tetrahalide of the formula III as the solvent. The amount of solvent relative to compound of the formula II may vary within a wide range and may be from 100 to 2,000% by weight, advantageously from 300 to 1,000% by weight, based on carboxylic acid amide.

The reaction of the carboxylic acid amide of the formula II with the carbon tetrahalide of the formula III to give an iminium salt of the formula IV is carried out at from room temperature to 120° C., under atmospheric or superatmospheric pressure, batchwise or continuously.

If the reaction is carried out with carbon tetrachloride, it takes place at from 90° to 120° C., preferably from 100° to 110° C., whilst when using carbon tetrabromide or bromotrichloromethane, it is carried out at from room temperature to 120° C., preferably from 20° to 100° C.

The iminium salts of the formula IV obtained by reacting a carboxylic acid amide of the formula II with a carbon tetrahalide of the formula III are novel compounds. In formula IV, X is halogen, preferably chlorine or bromine, and the halogen substituents of the vinyl group may differ from one another and from the anion. $R^1$ and $R^2$ in formula IV are each alkyl of 1 to 4 carbon atoms, especially methyl. $R^3$ and $R^4$ may be alkyl of 1 to 4 carbon atoms, especially methyl, ethyl or isopropyl, aralkyl of 7 to 9 carbon atoms, especially benzyl, or aryl of 6 to 10 carbon atoms, especially phenyl. $R^3$ and $R^4$ may also, together with the nitrogen on which they are present as substituents, form a 5-membered or 6-membered ring which may contain a further hetero-atom, especially oxygen. Examples of such rings are pyrrolidine, piperidine and morpholine.

The iminium salts of the formula IV can be converted to the compounds of the formula I by treatment with an equal to 20-fold, preferably a 5-fold to 10-fold, amount by weight of water at from 20° to 150° C., preferably from 80° to 100° C., under atmospheric or superatmospheric pressure. This hydrolysis may be carried out in the presence of the organic diluent or solvent in whose presence the iminium salt was synthesized. The resulting tetrahydrofurananones of the formula I can be isolated in a conventional manner by separating them from the aqueous phase or by extraction from the aqueous reaction mixture, and can be purified by distillation or crystallization.

The Examples which follow illustrate the process according to the invention.

EXAMPLE 1

A mixture of 250 ml of cyclohexane, 15.5 g (0.1 mole) of 3,3-dimethyl-pent-4-enoic acid N,N-dimethylamide, 33.2 g (0.1 mole) of carbon tetrabromide and 2.4 g (0.01 mole) of dibenzoyl peroxide is stirred for 5 hours at 80°–85° C. After distilling off the cyclohexane and 5 g of unconverted 3,3-dimethyl-pent-4-enoic acid N,N-dimethylamide, N,N-dimethyl-[5-(2,2,2-tribromoethyl)-4,4-dimethyltetrahydrofur-2-yl]-iminium bromide is obtained as a crystalline residue. This is stirred with 100 ml of water for 1 hour at 80°–90° C. and the mixture is then extracted with methylene chloride. After distilling the methylene chloride from the extract, 19 g of 5-(2,2,2-tribromoethyl)-4,4-dimethyl-tetrahydrofuran-2-one, of melting point 102°–102.5° C., are obtained.

$C_8H_{11}O_2Br_3$ (379): calculated: C 25.33% H 2.9% Br 63.3%. found: C 25.5% H 2.9% Br 63.2%.

NMR (80 MHz): 1.05 ppm (s; 3H); 1.25 ppm (s; 3H); 2.4 ppm (d; 2H); 3.32 ppm (d; 2H); 4.3 ppm (t; 1H).

EXAMPLE 2

A solution of 31 g (0.2 mole) of 3,3-dimethyl-pent-4-enoic acid N,N-dimethylamide in 120 g (0.6 mole) of bromotrichloromethane and 200 ml of carbon tetrachloride is irradiated for 15 hours, at 20° C., with a 300 W mercury high-pressure lamp. After distilling off the volatile constituents under reduced pressure at not above 30° C., the reaction mixture which remains is stirred with 300 ml of petroleum ether. This precipitates 51 g of N,N-dimethyl-[5-(2,2,2-trichloroethyl)-4,4-dimethyl-tetrahydrofur-2-yl]-iminium bromide. The hygroscopic substance melts at 190°–191° C.

$C_{10}H_{17}ONCl_3Br$ (354): calculated: N 3.96% Cl 30.09% Br 22.6% (ionic). found: N 4.0% Cl 29.2% Br 23.8% (ionic).

NMR (80 MHz): 1.25 ppm (s; 3H); 1.4 ppm (s; 3H); 2.9–4.0 ppm (mp; 4H); 3.45 ppm (s; 3H); 3.6 ppm (s; 3H); 5.3 ppm (d; 1H).

EXAMPLE 3

31 g (0.2 mole) of 3,3-dimethyl-pent-4-enoic acid N,N-dimethylamide and 4.6 g (0.02 mole) of tert.-butyl 2-ethyl-hexanepercarboxylate are added continuously to a solution of 120 g (0.6 mole) of bromotrichloromethane in 250 ml of cyclohexane whilst stirring at 85° C. Stirring is then continued at the same temperature for 2 hours. 28 g of N,N-dimethyl-[5-(2,2,2-trichloroethyl)-4,4-dimethyl-tetrahydrofur-2-yl]-iminium bromide, of melting point 190°–191° C., crystallize out.

After concentrating the filtrate and adding 200 ml of petroleum ether, a further 31 g of N,N-dimethyl-[5-(2,2,2-trichloroethyl)-4,4-dimethyl-tetrahydrofur-2-yl]-iminium bromide are obtained.

EXAMPLE 4

A solution of 31 g (0.2 mole) of 3,3-dimethyl-pent-4-enoic acid N,N-dimethylamide and 66.4 g (0.2 mole) of carbon tetrabromide in 260 ml of carbon tetrachloride is irradiated for 7 hours at 20° C. by means of a 300 W mercury high-pressure lamp. After distilling the volatile constituents from the reaction mixture, a crystalline residue is obtained. This is stirred with 100 ml of chloroform, filtered off and dried, to give 30 g (0.06 mole) of N,N-dimethyl[5-(2,2,2-tribromoethyl)-4,4-dimethyltetrahydrofur-2-yl]-iminium bromide, of melting point 169°–169.5° C.

$C_{10}H_{17}ONBr_4$ (487): calculated: C 24.67% H 3.52% N 2.88% Br (total) 65.65% Br (ionic) 16.4%. found: C 24.8% H 3.6% N 2.9% Br (total) 65.1% Br (ionic) 16.1%.

NMR (80 MHz): 1.1 ppm (s; 3H); 1.28 ppm (s; 3H); 3.2 ppm (d; 2H); 3.24 ppm (s; 3H); 3.26 ppm (s; 3H); 3.55 ppm (d; 2H); 4.92 ppm (t; 1H).

EXAMPLE 5

77 g (0.5 mole) of 3,3-dimethyl-pent-4-enoic acid N,N-dimethylamide, 130 g (0.84 mole) of carbon tetrachloride, 35 g of acetonitrile, 0.85 g (0.005 mole) of $CuCl_2.2H_2O$ and 1 g of diethylammonium chloride are stirred for 12 hours at 100° C., under a pressure of 5 bar, in a stainless steel stirred autoclave. Acetonitrile and excess carbon tetrachloride are then distilled from the reaction mixture under reduced pressure. This leaves 163 g of a semi-crystalline mass which is insoluble in carbon tetrachloride and which, according to elementary analysis and according to a mass spectrum, substantially consists of N,N-dimethyl-[5-(2,2,2-trichloroethyl)-4,4-dimethyl-tetrahydrofur-2-yl]-iminium chloride. The product is treated with 500 ml of water at 20° C. and the mixture is extracted with carbon tetrachloride. After stripping off the solvent, distillation of the residue gives 24 g of 5-(2,2,2-trichloroethyl)-4,4-dimethyl-tetrahydrofuran-2-one, of boiling point 111°–115° C./0.013 mbar and melting point 56°–58° C.

$C_8H_{11}O_2Cl_3$ (246): calculated: C: 39.13% H: 4.52% O: 13.03% Cl: 43.32%. found: C: 39.6% H: 4.8% O: 13.1% Cl: 42.6%.

NMR (100 MHz): 1.02 ppm (s; 3H); 1.21 ppm (s; 3H); 2.38 ppm (dd; 2H); 2.98 ppm (d; 2H); 4.45 ppm (t; 1H).

We claim:

1. A process for the preparation of a 5-(2,2,2-trihaloethyl)-4,4-dialkyl-tetrahydro-furan-2-one of the formula I

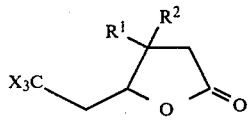

where $R^1$ and $R^2$ are each alkyl of 1 to 4 carbon atoms and X is halogen, wherein a carboxylic acid amide of the formula II

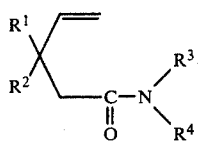

where $R^1$ and $R^2$ are each alkyl of 1 to 4 carbon atoms and $R^3$ and $R^4$ are each alkyl of 1 to 4 carbon atoms, aralkyl of 7 to 9 carbon atoms or aryl of 6 to 10 carbon atoms, or together with the nitrogen atom on which they are present as substituents form a 5-membered or 6-membered saturated ring which may contain a second hetero-atom, is reacted with a carbon tetrahalide of the formula III $$CX_4 \qquad (III)$$

where X is halogen, in the presence of an initiator and of an organic diluent or solvent, at from room temperature to 120° C., to give an iminium salt of the formula IV

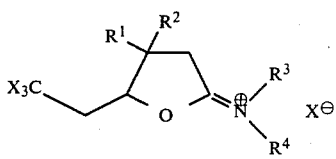

where $R^1$, $R^2$, $R^3$, $R^4$ and X have the above meanings, and this iminium salt is subsequently hydrolyzed.

2. A process as set forth in claim 1, wherein $R^3$ and $R^4$ together with the nitrogen atom on which they are present as substituents form a pyrrolidine, piperidine or morpholine ring.

3. A process as set forth in claim 1, wherein $R^3$ and $R^4$ are each alkyl of 1 to 4 carbon atoms, aralkyl of 7 to 9 carbon atoms or aryl of 6 to 10 carbon atoms.

* * * * *